(12) United States Patent
Lee

(10) Patent No.: US 11,241,315 B2
(45) Date of Patent: Feb. 8, 2022

(54) 3-DIMENSIONAL BLOCK TYPE BONE GRAFT

(71) Applicant: EZEKIEL CO., LTD, Chungcheongnam-do (KR)

(72) Inventor: Jaejoon Lee, Chungcheongnam-do (KR)

(73) Assignee: EZEKIEL CO., LTD, Chungcheongnam-Do (KR)

( * ) Notice: Subject to any disclaimer, the term of this patent is extended or adjusted under 35 U.S.C. 154(b) by 539 days.

(21) Appl. No.: 16/157,656

(22) Filed: Oct. 11, 2018

(65) Prior Publication Data

US 2019/0038413 A1    Feb. 7, 2019

Related U.S. Application Data

(63) Continuation-in-part of application No. 14/556,006, filed on Nov. 28, 2014, now abandoned.

(51) Int. Cl.
*A61F 2/00* (2006.01)
*A61F 2/28* (2006.01)
*A61F 2/30* (2006.01)

(52) U.S. Cl.
CPC ........ *A61F 2/28* (2013.01); *A61F 2002/2835* (2013.01); *A61F 2002/3092* (2013.01); *A61F 2002/30199* (2013.01); *A61F 2002/30303* (2013.01); *A61F 2002/30593* (2013.01)

(58) Field of Classification Search
CPC ............... A61F 2/28; A61F 2002/2835; A61F 2002/3092; A61F 2002/30303; A61F 2002/30593; A61F 2002/30199; A61B 5/0036; A61B 6/032; C12N 5/0654; C12N 5/0068; C12N 2535/00; C12N 2513/00; C12N 2533/18
See application file for complete search history.

(56) References Cited

U.S. PATENT DOCUMENTS

2003/0065400 A1 *   4/2003   Beam ................... C04B 35/638
                                                      623/23.51

* cited by examiner

*Primary Examiner* — Marcia S Noble
*Assistant Examiner* — Lauren K Van Buren
(74) *Attorney, Agent, or Firm* — The PL Law Group, PLLC

(57) ABSTRACT

A 3-dimensional block type bone graft includes a plurality of first channels extending horizontally in forward and backward directions and arranged at a predetermined interval in left and right directions and upward and downward directions, a plurality of second channels extending horizontally in the left and right directions and arranged at a predetermined interval in the forward and backward directions and the upward and downward directions, and a plurality of third channels extending vertically in the upward and downward directions and arranged at a predetermined interval in the forward and backward directions and the left and right directions, wherein the first channels, the second channels, and the third channels intersect perpendicularly to each other to communicate with each other so that the first channels, the second channels, and the third channels are configured in a 3-dimensional shape.

4 Claims, 6 Drawing Sheets

FIG. 1
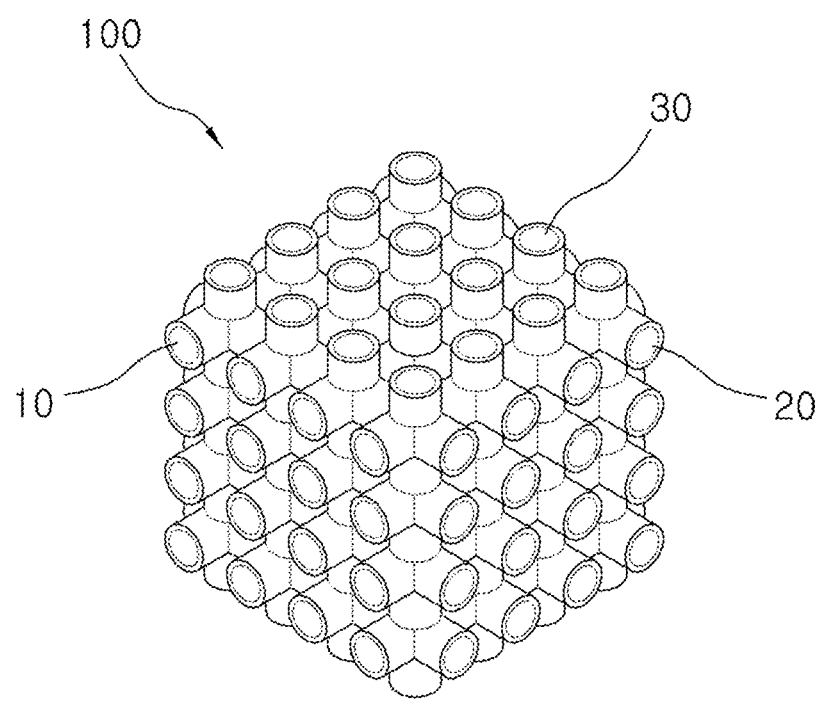
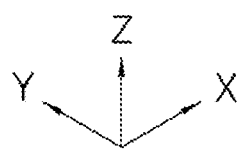

FIG. 3
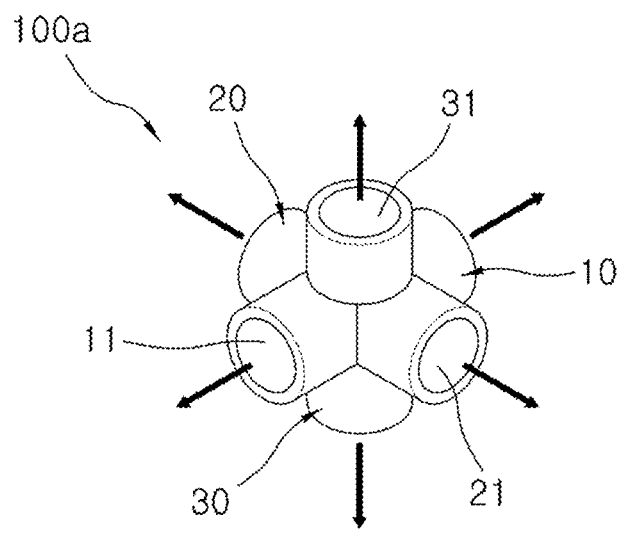
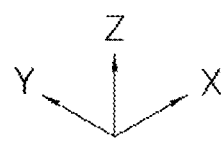
FIG. 4
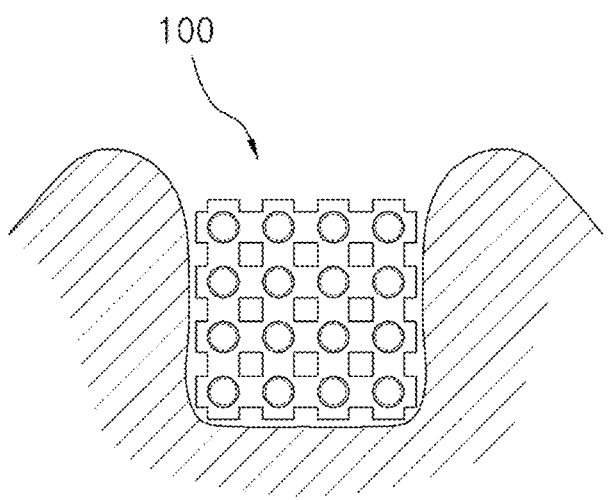

3-DIMENSIONAL BLOCK TYPE BONE GRAFT

CROSS-REFERENCE TO RELATED APPLICATION AND CLAIM OF PRIORITY

This application is a Continuation-In-Part of co-pending application Ser. No. 14/556,006 filed on Nov. 28, 2014, the entire contents of all are hereby incorporated by reference.

BACKGROUND

1. Field of the Invention

The present invention relates to a bone graft used in a bone defect.

2. Description of the Related Art

Bone tissue is the only hard tissue in a living body, and a region where the bone tissue is damaged is filled with a bone to create a new bone. Methods for recovery of such bone defects include autografting, allografting, and xenografting.

Although the autografting does not have the concern of infection or immune rejection, the autografting requires a secondary surgery and may hardly provide a required amount of bone tissues. In addition, the allografting has the concern of immune rejection and secondary infection, and the xenografting has problems of immune rejection and slow bone formation.

Accordingly, a bone graft has been developed to be easily provided in a sufficient amount, to have no possibility of disease transmission, to have excellent biocompatibility, and to be properly absorbed after the grafting so as to be replaced with a regenerated bone. Such a bone graft is mainly formed of calcium phosphate compounds having components similar to inorganic components of a bone, such as hydroxyapatite (HA) and β-tricalcium phosphates (β-TCP).

However, since a conventional bone graft formed of the calcium phosphate compounds is mainly provided as powder, the conventional bone graft has limitations in that the bone graft may be spilled from a bone defect during the grafting, causing a large loss of the bone graft and making it difficult to perform the grafting while requiring a long time, and the bone graft has insufficient porosity so that slow blood absorption into the bone graft may occur and an effective space for allowing a bone to grow therein may be insufficient, resulting in ineffective bone formation.

SUMMARY

To solve the conventional problems described above, an object of the present invention is to provide a 3-dimensional block type bone graft which is not spilled out, so that the grafting is performed more simply and conveniently, and bone formation is effectively performed.

To achieve the object described above, according to the present invention, there is provided a 3-dimensional block type bone graft including: a plurality of first channels extending horizontally in forward and backward directions and arranged at a predetermined interval in left and right directions and upward and downward directions; a plurality of second channels extending horizontally in the left and right directions and arranged at a predetermined interval in the forward and backward directions and the upward and downward directions; and a plurality of third channels extending vertically in the upward and downward directions and arranged at a predetermined interval in the forward and backward directions and the left and right directions, wherein the first channels, the second channels, and the third channels intersect perpendicularly to each other to communicate with each other so that the first channels, the second channels, and the third channels are configured in a 3-dimensional shape.

In this case, the first channel, the second channel, and the third channel may have an inner diameter of 300 μm to 1,000 μm, and the first channels, the second channels, and the third channels may be arranged at an interval of 200 μm to 1,000 μm, respectively.

According to the present invention, the bone graft is not spilled from a grafting site, so that the grafting can be performed more simply and conveniently without loss of the bone graft.

In addition, the present invention provides excellent porosity, allows fast blood circulation, and sufficiently provides an effective space for allowing surrounding bones to grow therein, so that the bone formation can be effectively performed through excellent osteoinduction and osteoconduction.

In addition, the bone graft can be broken down to small pieces and rearranged into a new form as necessary, so that volume maintenance and sealing effects can be obtained.

BRIEF DESCRIPTION OF THE DRAWINGS

FIG. 1 is a view showing a 3-dimensional shape of a bone graft according to one example of the present invention.

FIG. 3 is a view illustrating one separated intersection point of the bone graft.

FIG. 4 is a view illustrating a state in which the bone graft is inserted into a bone defect.

DETAILED DESCRIPTION

Hereinafter, a 3-dimensional block type bone graft according to embodiments of the present invention will be described in detail with reference to the accompanying drawings.

Figure 2:
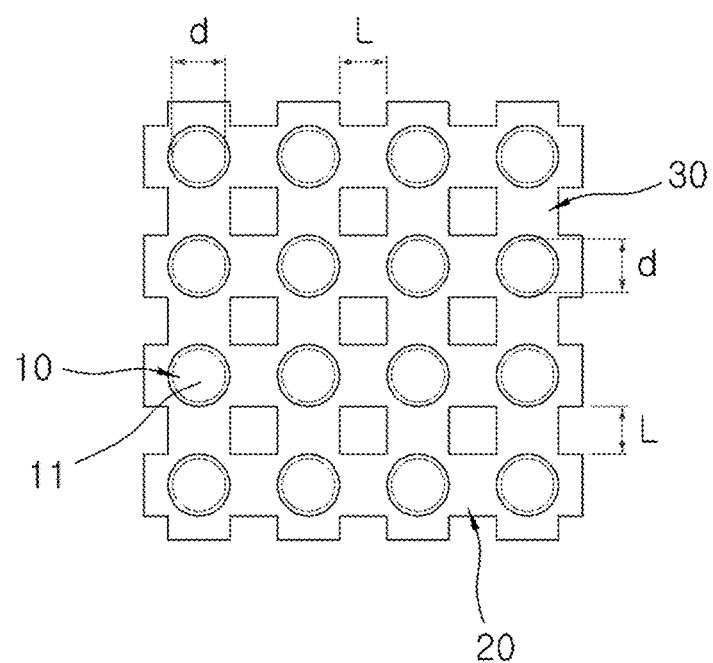
FIG. 2 is a front view showing the bone graft according to one example of the present invention.

As illustrated in FIGS. 1 and 2, a 3-dimensional block type bone graft 100 according to the present invention includes a plurality of first channels 10, second channels 20, and third channels 30, which are configured in a 3-dimensional shape.

The bone graft 100 according to the present invention is formed of a mixture of hydroxyapatite (HA) and β-tricalcium phosphates (β-TCP), and a mixing ratio of HA and β-TCP is preferably 6:4.

The channels included in the present invention denote tubes having a hollow passage to allow blood to be circulated through an inside of the tube, and the first channels 10, the second channels 20, and the third channels 30 are distinguished from each other according to extension directions thereof.

In other words, the first channel 10 is a channel formed therein with a passage 11 and extending horizontally in forward and backward directions (X-axis direction in FIG. 1).

The second channel 20 is a channel formed therein with a passage 21 and extending horizontally in left and right directions (Y-axis direction in FIG. 1).

The third channel 30 is a channel formed therein with a passage 31 and extending vertically in upward and downward directions (Z-axis direction in FIG. 1).

As illustrated in FIG. 1, the first channels 10, the second channels 20, and the third channels 30 extending in different extension directions are arranged in an X-Y-Z 3-dimensional matrix structure and integrated perpendicularly to each other so as to form a 3-dimensional block.

In other words, the first channels 10 are arranged at a predetermined interval in the left and right directions (Y-axis direction) and the upward and downward directions (Z-axis direction), the second channels 20 are arranged at a predetermined interval in the forward and backward directions (X-axis direction) and the upward and downward directions (Z-axis direction), and the third channels 30 are arranged at a predetermined interval in the forward and backward directions (X-axis direction) and the left and right directions (Y-axis direction).

In addition, the first channels 10, the second channels 20, and the third channels 30 arranged as described above intersect perpendicularly to each other to communicate with each other so as to form a 3-dimensional block having an X-Y-Z 3-dimensional channel structure.

In such a 3-dimensional block, as illustrated in FIG. 3, the passages 11, 21, and 31 of the first channels 10, the second channels 20, and the third channels 30 communicate with each other at an intersection point, so that the blood can be circulated in six directions, which are the forward, backward, left, right, upward, and downward directions, based on the intersection point.

In this case, inner diameters d of the first channel 10, the second channel 20, and the third channel 20, that is, diameters of the passages 11, 21, and 31 are set to 300 μm to 1,000 μm. In addition, the first channel 10, the second channel 20, and the third channel 20 may have an identical inner diameter or different inner diameters.

In addition, the first channels 10, the second channels 20, and the third channels 30 are preferably arranged at an interval L of 200 μm to 1,000 μm, respectively.

Although the 3-dimensional block having a cubic shape has been described with reference to the accompanying drawings in the above description, the embodiment is provided for convenience of explanation, and the 3-dimensional block may have various shapes such as a rectangular shape, a spherical shape, a cylindrical shape, and a disc shape without limitation.

The bone graft having the above-described configuration according to the present invention is provided as a standardized 3-dimensional block having the 3-dimensional channel structure. Accordingly, when the bone graft is inserted into a bone defect as illustrated in FIG. 4, unlike an existing powder type bone graft, the bone graft is not spilled from a grafting site, so that the grafting can be performed more simply and conveniently without loss of the bone graft.

In addition, the bone graft of the present invention is a scaffold serving as a matrix, and has the X-Y-Z 3-dimensional channel structure with excellent porosity, in which the blood is circulated in the six directions through the channel structure, so that absorption and migration of the blood and cells can be performed rapidly.

Further, since an inner space is provided in each of the channels and an outer space is provided between the channels, an effective space for allowing surrounding bones to grow therein may be sufficient, so that bone formation can be effectively performed through excellent osteoinduction and osteoconduction.

Figure 5:
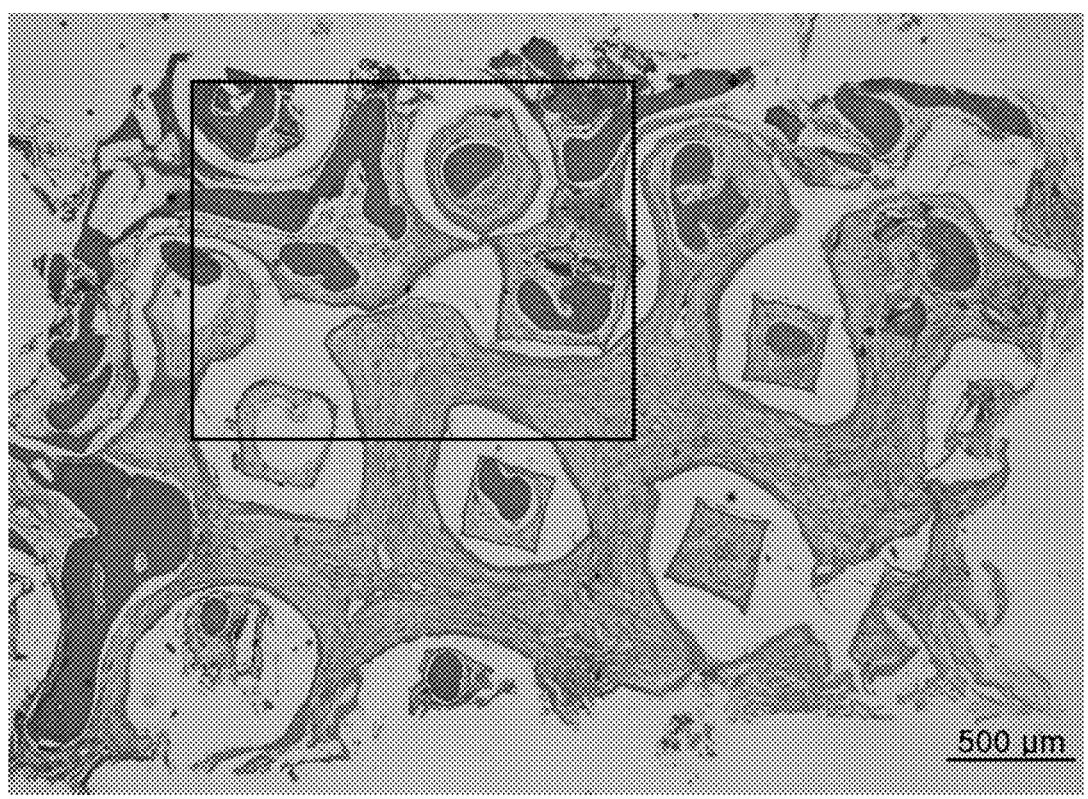
FIGS. 5 and 6 are views showing tissue biopsies of a specimen after grafting the bone graft.
Figure 6:
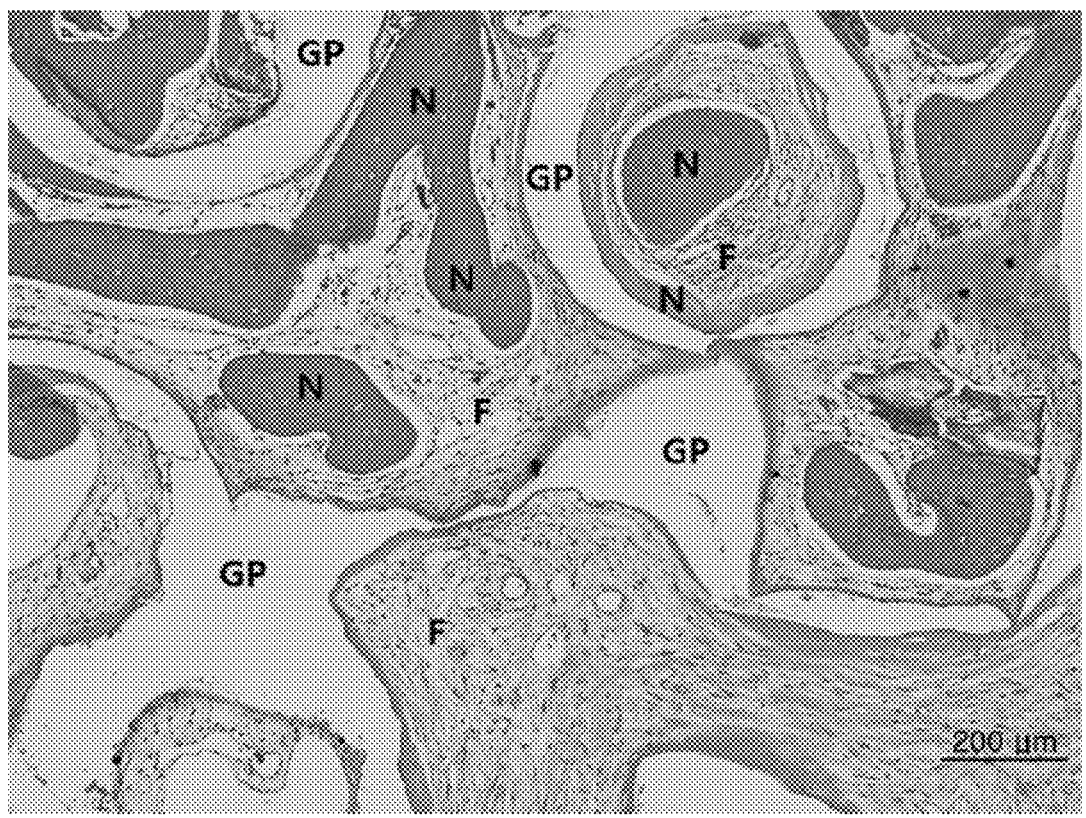

FIG. 5 shows a biopsy of a decalcified specimen obtained by grafting the bone graft of the present invention into the bone defect and decalcifying the specimen after about 5 months, and FIG. 6 is an enlarged view showing a rectangular portion of FIG. 5. Since the specimen is decalcified, a bone graft GP is eliminated and observed as an empty space, and it is observed that a new bone N and a fibrous tissue F are grown and formed around an inner center of the empty space, around a wall defining the empty space, and at an outside of the empty space.

Figure 7:
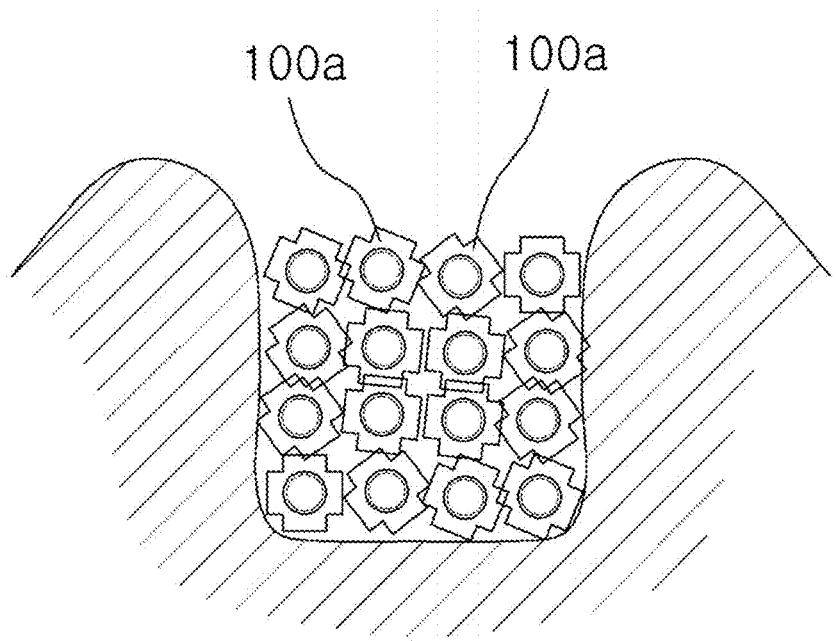
FIG. 7 is a view illustrating a state in which the bone graft is inserted and broken down into unit channel members.

Meanwhile, the bone graft of the present invention can be broken down to small pieces and rearranged into a new form as illustrated in FIG. 7 in addition to a grafting scheme in which the 3-dimensional block is used as illustrated in FIG. 4.

In other words, according to structural features that the channels 10, 20, and 30 extend perpendicularly to each other in three directions, which are X-Y-Z directions, while the channels 10, 20, and 30 are respectively arranged at a predetermined interval L, the bone graft of the present invention has a strength difference between an intersecting portion and a portion which interconnects intersecting portions.

Therefore, when the bone graft is inserted into the bone defect and a predetermined force is applied thereto, connecting portions with relatively weak strength other than the intersecting portions are broken, so that the bone graft may be broken down into a plurality of unit channel members 100a having a configuration in which channels intersect with each other in the X-Y-Z directions as illustrated in FIG. 3. As described above, when the 3-dimensional block is inserted into the bone defect and broken down into the unit channel members 100a as shown in FIG. 7, volume maintenance and sealing effects are improved.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A 3-dimensional block type bone graft comprising:
   a plurality of first channels extending horizontally in forward and backward directions and separated from each other at predetermined intervals;
   a plurality of second channels extending horizontally at left and right directions and separated from each other at predetermined intervals; and
   a plurality of third channels extending vertically in upward and downward directions and separated from each other at predetermined intervals,
   wherein the first channels, the second channels, and the third channels intersect perpendicularly to each other, and each protrude outward from the 3-dimensional block type bone graft.

2. The 3-dimensional block type bone graft of claim 1, wherein the first channels, the second channels, and the third channels have an inner diameter of 300 μm to 1,000 μm.

3. The 3-dimensional block type bone graft of claim 2, wherein the first channels, the second channels, and the third channels are arranged at an interval of 200 μm to 1,000 μm, respectively.

4. The 3-dimensional block type bone graft of claim 1, wherein the first, second, and third channels comprise porous material selected from the group consisting of hydroxyapatite (HA), β-TCP (tricalcium phosphate), and mixtures thereof.

\* \* \* \* \*